United States Patent [19]

Arai et al.

[11] Patent Number: 5,183,741

[45] Date of Patent: Feb. 2, 1993

[54] INTEGRAL MULTILAYER ELEMENT FOR GLUCOSE ANALYSIS

[75] Inventors: Fuminori Arai; Harumi Katsuyama, both of Asaki, Japan

[73] Assignee: Fuji Photo Film Co., Ltd., Kanagawa, Japan

[21] Appl. No.: 603,243

[22] Filed: Oct. 22, 1990

Related U.S. Application Data

[63] Continuation of Ser. No. 387,397, Jul. 27, 1989, abandoned, which is a continuation of Ser. No. 262,159, Oct. 19, 1988, abandoned, which is a continuation of Ser. No. 97,304, Sep. 14, 1987, abandoned, which is a continuation of Ser. No. 660,658, Oct. 15, 1984, abandoned.

[30] Foreign Application Priority Data

Oct. 13, 1983 [JP] Japan ................ 58-191246

[51] Int. Cl.$^5$ .......... C12Q 1/54; C12Q 1/26; C12Q 1/28; C12N 11/18
[52] U.S. Cl. .................. 435/14; 435/25; 435/28; 435/174; 435/175; 435/176; 435/180; 435/805; 422/56; 422/57
[58] Field of Search ............ 435/14, 25, 28, 174, 435/175, 176, 180, 805; 422/56, 57

[56] References Cited

U.S. PATENT DOCUMENTS

| | | | |
|---|---|---|---|
| 2,983,005 | 9/1976 | Goudhue et al. | 435/23 X |
| 3,992,158 | 11/1976 | Przybylowicz et al. | 435/28 X |
| 4,042,335 | 8/1977 | Clement | 422/56 |
| 4,166,763 | 9/1979 | Esders et al. | 435/28 |
| 4,292,272 | 9/1981 | Kitajima et al. | 422/56 X |
| 4,452,887 | 6/1984 | Kitajima et al. | 422/56 X |
| 4,478,942 | 10/1984 | Katsuyama et al. | 435/28 X |
| 4,503,145 | 3/1985 | Katsuyama et al. | 435/28 X |
| 4,578,245 | 3/1986 | Arai et al. | 422/56 |
| 4,604,347 | 8/1986 | Arai et al. | 435/4 |

FOREIGN PATENT DOCUMENTS 2104215 3/1983 United Kingdom.

*Primary Examiner*—David M. Naff
*Attorney, Agent, or Firm*—McAulay Fisher Nissen Goldberg & Kiel

[57] ABSTRACT

An integral multilayer element for chemical analysis utilizing an oxidase enzyme reaction system is prepared having in the following order:

(a) a porous spreading layer;
(b) an oxygen-permeable, protein-impermeable light-blocking layer;
(c) an oxidase-containing layer;
(d) an indicator layer containing peroxidase and a hydrogen peroxide indicator showing detectable change in the presence of peroxidase and hydrogen peroxide; and
(e) a water-impermeable, light-transmissive support.

The oxidase in the oxidase-containing layer is preferably glucose oxidase to provide a multilayer element for glucose determination. This multilayer element shortens the analytical time, widens the measurable concentration range of the analyte and improves accuracy.

5 Claims, No Drawings

INTEGRAL MULTILAYER ELEMENT FOR GLUCOSE ANALYSIS

This is a continuation of application Ser. No. 387,397, filed Jul. 27, 1989, now abandoned which, in turn, is a continuation of application Ser. No. 262,159, filed Oct. 19, 1988, now abandoned, which, in turn, is a continuation of application Ser. No. 097,304, filed Sep. 14, 1987, now abandoned, which, in turn, is a continuation of application Ser. No. 660,658, filed Oct. 15, 1984, now abandoned.

BACKGROUND OF THE INVENTION

1. Field of The Invention

The present invention relates to an integral multilayer element for chemical analysis. More particularly, this invention relates to an integral multilayer element for chemical analysis suitable for use in performing quantitative analysis for substances contained in aqueous liquid samples, particularly biological fluids such as blood, lymph fluid, spinal fluid, urine, etc., utilizing an oxidase enzyme reaction system which produces hydrogen peroxide upon reaction.

2. Description of Prior Arts

There have been proposed and practically used integral multilayer elements for chemical analysis (hereinafter referred to often as multilayer analytical element) in the form of film or sheet as a dry analytical instrument for performing quantitative analysis on a analyte (substance to be analyzed), according to the principle that an analyte or a reaction product thereof is oxidized by an oxidas, subsequently the formed $H_2O_2$ is involved in a dye-forming reaction in the presence of peroxidase and the formed dye is determined colormetrically.

As reagents for conducting the dye-forming reaction using oxidase and peroxidase, there are known reagents proposed by P. Trinder in the literature "Annals for Clinical Biochemistry," 6, 24–27 (1969) and their improved reagents which are generally employed in the conventional multilayer analytical element. The improved Trinder reagent is a dye-forming indicator composition containing an oxidase; peroxidase; a hydrogen donor (chromogen) such as 4-aminoantipyrine or a 4-aminoantipyrine homologue or a derivative, e.g., 4-amino-2-methyl-3-phenyl-1-(2,4,6-trichlorophenyl)-3-pyrazolin-5-one; and a coupler such as hydroxynaphthalene, e.g., 1,7-dihydroxynaphthalene, sodium 1-hydroxynaphthalene-2-sulfonate or the like. The reagents proposed by Trinder and the improved reagents (hereinafter both referred to simply as Trinder reagent) have an advantage that if the kind of the oxidase is changed, the whole remaining components can be used as the dye-forming indicator composition.

It is known that glucose oxidase, cholesterol oxidase, uricase, glycerol oxidase, etc. can be used as the oxidase. It is also known that in the dye-forming indicator composition containing the oxidase and peroxidase, dianisidine or a colorless leuco-dye such as 4,5-bis[4-(dimethylamino)phenyl]-2-(4-hydroxy-3,5-dimethoxyphenyl)imidazole serving as a hydrogen donor can be used instead of a combination of a hydrogen donor (chromogen) and a coupler (see, U.S. Pat. No. 3,992,158, Japanese Patent Publications No. 55(1980)-25840 (U.S. Pat. No. 3,886,045 and FR 2,185,289), No. 56(1981)-45599 (U.S. Pat. No. 3,983,005), and No. 57(1982)-5519 (U.S. Pat. No. 4,089,747), etc.).

In a multilayer analytical element containing the Trinder reagent, an analyte dissolved in an aqueous liquid reaches a reagent layer where the analyte is reacted with oxygen ($O_2$) in air under catalystic action of an oxidase to form $H_2O_2$, and an oxidation-coupling reaction (oxidative color reaction) then proceeds under the catalytic action of peroxidase to generate or change a color. Hence, oxygen in air is an essential component for performing the reaction among a series of coupled reactions taking place in the multilayer analytical element. For this reason, there has been proposed that the oxidase is incorporated into a layer positioned above a layer containing the remaining components of the Trinder reagent (layer positioned far away from the support) to accelerate the progress of the color reaction (i.e., dye-forming reaction) and at the same time to improve the analytical accuracy (see, Japanese Patent Provisional Publication No. 57(1982)-208997 (GB 2,104,215A)). It has been found that the incorporation of the oxidase in a layer positioned above a layer containing the remaining components of the Trinder reagent has a remarkable effect of accelerating the progress of the color reaction and improving the analytical accuracy in the multilayer analytical element where a porous spreading layer and a nonporous blocking layer are provided in this order on a reagent layer containing the Trinder reagent described in Japanese Patent Provisional Publication No. 55(1980)-164356 (U.S. Pat. No. 4,292,272), etc.

However, it has been also found that in the multilayer analytical element where the oxidase is incorporated into a layer positioned above a layer containing the remaining components of the Trinder reagent, there is a disadvantage that the analytical accuracy is deteriorated by the interference of an oxidation-reduction interfering substance contained in an aqueous liquid sample spotted on a porous spreading layer. The term "oxidation reduction interfering substance" used herein refers to ascorbic acid or other material having hydrogen peroxide-decomposing activity such as catalase, hemoglobin, etc. (the term "hydrogen peroxide-decomposing activity" used herein refers to either or both of catalase activity and peroxidase activity) when the aqueous liquid sample is a biological body fluid. Further, it has been found that the above-mentioned disadvantage takes place remarkably when whole blood, hemolyzed whole blood, plasma or serum is used as the aqueous liquid sample.

SUMMARY OF THE INVENTION

An object of the present invention is to shorten analytical time and to widen the measurable concentration range of the analyte with an improvement in the analytical accuracy by eliminating negative errors, etc. caused by the interference of an oxidation-reduction interfering substance contained in the aqueous liquid sample in the procedure of using an integral multilayer element for chemical analysis containing an oxidase, peroxidase, a hydrogen donor (chromogen) and a coupler (or a hydrogen donor which is single compound capable of generating or changing a color by oxidation in place of a combination of the hydrogen donor and the coupler) as essential components and in which the oxidase is incorporated in a layer positioned above a layer containing the remaining components (the layer containing the oxidase positioned far away from the support).

Another object of the invention is to shorten the analytical time and to widen the measurable concentration range of the analyte in the case of analysis of a blood (whole blood, plasma or serum) with an improvement in the analytical accuracy by reducing or eliminating the interference caused by conjugated protein, such as catalase, hemoglobin or the like, which has hydrogen peroxide-decomposing activity and is an oxidation-reduction interfering substance in the blood resulting from hemolysis when the blood is used as the aqueous liquid sample.

The objects of the present invention are attained by interposing an oxidase-containing layer between a layer containing the remaining components and the oxygen-permeable, proten-impermeable light-blocking layer in the multilayer analytical element.

Accordingly, the present invention provides an integral multilayer element for chemical analysis comprising in order:

(a) a porous spreading layer;

(b) an oxygen-permeable, protein-impermeable light-blocking layer;

(c) an oxidase-containing layer;

(d) an indicator layer containing peroxidase and a hydrogen peroxide indicator showing detectable change in the presence of peroxidase and hydrogen peroxide; and (e) a water-impermeable, light-transmissive support.

The oxidase-containing layer can further contain a mordant.

The integral multilayer element for chemical analysis of the present invention is characterized in that a layer containing an oxidase or a layer containing an oxidase and a mordant is provided between the oxygen-permeable, protein-impermeable light-blocking layer and the indicator layer.

DETAILED DESCRIPTION OF THE INVENTION

As the water-impermeable, light-transmissive support of the invention, there may be used any of supports for the multilayer analytical elements described in Japanese Patent Publication No. 53(1978)-21677 (U.S. Pat. No. 3,992,158), Japanese Patent Provisional Publication No. 55(1980)-164356 (U.S. Pat. No. 4,292,272), etc. Examples of such supports include transparent films or sheets of approx. 50 μm to 1 mm, preferably approx. 80 μm to 400 μm in thickness made of less hydrophilic or hydrophobic polymers such as cellulose acetate, cellulose acetate butyrate, poly(ethylene terephthalate), bisphenol A polycarbonate, polystyrene, polymethyl methacrylate, etc. and transparent glass plate of approx. 100 μm to 2 mm, preferably approx. 150 μm to 1 mm in thickness. If desired, the surface of the support may be subjected to a physical or chemical treatment such as ultraviolet light irradiation, corona discharge treatment or the like to enforce adhesion to the indicator layer, etc. Alternatively, a hydrophilic polymer subbing layer composed of a gelatin or the like may be provided on the surface of the support after (or without) the physical or chemical treatment of said surface.

The indicator layer means a layer containing peroxidase and a hydrogen peroxide indicator showing detectable change in the presence of peroxidase and hydrogen peroxide, and peroxidase dispersed or dissolved in a polymer binder having a hydrophilic film-forming property. As the hydrogen peroxide indicator, there can be used a combination of a hydrogen donor (chromogen) and a phenol coupler or a naphthol coupler described in the literature "Annals of Clinical Chemistry", 6, 24–27(1969), U.S. Pat. No. 3,992,158, Japanese Patent Publications No. 55(1980)-25840, No. 56(1981)-45599, and No. 58(1983)-18628 (U.S. Pat. No. 4,042,335) and Japanese Patent Application No. 57(1982)-165233 (Japanese Patent Provisional Publication No. 59(1984)-54962 and EP 0 103 903A), etc., triarylimidazole leuco-dyes described in Japanese Patent Publication No. 57(1982)-5519, Japanese Patent Application No. 58(1983)-68009, etc., and single compounds which are dye precursor compounds capable of generating or changing a color by self-coupling in the presence of peroxidase and hydrogen peroxide described in Japanese Patent Publications No. 56(1981)-45599 and No. 58(1983)-18628, etc.

Preferred examples of the hydrogen peroxide indicators are as follows.

Combination of hydrogen donor (chromogen) and coupler:

Hydrogen donors: 4-aminoantipyrine homologues and derivatives such as 4-aminoantipyrine, 4-amino-2-methyl-3-phenyl-1-(2,4,6-trichlorophenyl)-3-pyrazolin-5-one, etc.

Couplers: 1-hydroxynaphthalene derivatives such as 1,7-dihydroxynaphthalene, sodium or potassium 1-hydroxynaphthalene-2-sulfonate, etc.

Triarylimidazole leuco-dyes:
4,5-bis[4-(dimethylamino)phenyl]-2-)4-hydroxy-3,5-dimethoxyphenyl)imidazole, 4-(dimethylamino)phenyl-2-(4-hydroxy-3,5-dimethoxyphenyl)-5-phenethylimidazole, etc.

Dye precursor compounds:
Dianisidine, 4-methoxy-1-naphthol, etc.

As the peroxidases, there can be used peroxidases originating from plant and animal (EC 1. 11. 1. 7) described in Japanese Patent Publication No. 56(1981)-45599 and No. 57(1982)-5520 (U.S. Pat. No. 4,211,845), etc. and peroxidases originating from microorganisms (EC 1. 11. 1. 7) described in Japanese Patent Publication No. 58(1983)-5035, etc. Among them, non-specific peroxidases originating from plant and microorganism are preferred. Examples of preferred peroxidases are those extracted from radish, horse radish and microorganisms of the genera Cochliobolus and Curvularia.

As the hydrophilic polymer binder used in the indicator layer, there can be used any of known hydrophilic polymers used as hydrophilic polymer binder for the reagent layers in the multilayer analytical elements described in Japanese Patent Publications No. 53(1978)-21677, No. 56(1981)-45599 and No. 57(1982)-5519, Japanese Patent Provisional Publications No. 55(1980)-164356 and No. 57(1982)-208997, etc. Examples of the hydrophilic polymer include gelatin (such as acid-treated gelatin, deionized gelatin, etc.), gelatin derivatives (such as phthalated gelatin, hydroxymethyl acrylate-grafted gelatin, etc.), pullulan, pullulan derivatives, agarose, polyvinyl alcohol, polyvinyl pyrrolidone, polyacrylamide, etc. Among them, gelatin is preferred.

The dry thickness of the indicator layer is within the range of approx. 5 μm to 60 μm, preferably approx. 10 μm to 30 μm. The peroxidase content of the indicator layer is within the range of approx. 5,000 to 100,000 U/m$^2$, preferably approx. 10,000 to 60,000 U/m$^2$. The amount of the hydrogen peroxide indicator in the indicator layer can be properly determined according to the estimated amount of analyte contained in the aqueous liquid sample.

A pH buffer may be incorporated in the indicator layer in order to keep the layer at the optimum pH value for the peroxidase or in the vicinity thereof, or to keep the layer at a pH at which the dye-forming (or color-changing) reaction of the hydrogen peroxide indicator rapidly proceeds without substantial interference by the activity of the peroxidase. The optimum pH value of the peroxidase varies depending on the origin thereof. For example, the optimum pH of the peroxidase originating from horse radish is 7.0, that of the peroxidase originating from Cochliobolus Miyabeanus is 5.0 to 5.3, and that of the peroxidase originating from Pellicularia Filamentosa is 4.7 to 4.9. Therefore, there can be incorporated in the indicator layer at a pH buffer capable of maintaining the indicator layer at a pH within the range of approx. 4.0 to 7.5, preferably approx. 4.5 to 7.0 under the analytical conditions. As the pH buffer, there can be used any of known pH buffers described in the following literatures: "Biochemistry", 5(2), 467–477(1966); R. M. C. Dawson et al. "Date for Biochemical Research" the second edition (Oxford at the Clarendon Press, 1969) pp. 476–508; "Analytical Biochemistry", 104, 300–310(1980); "Kagaku Binran Kiso-hen" pp 1312–1320, edited by the Japan Chemical Society (Maruzen, Tokyo, 1966); "Biochemistry Data Book I" pp. 17–24 edited by the Japan Biochemical Society (Tokyo Kagaku Dojin Ltd., 1979); Japanese Patent Publication No. 57(1982)-28277 (U.S. Pat. No. 4,098,574), etc.

The oxidase-containing layer is provided on the indicator layer directly or via an intermediate layer (described later). As the oxidase in the oxidase-containing layer, there can be used any of oxidases capable of catalyzing oxidation of the analyte with oxygen ($O_2$) to form $H_2O_2$. Examples of the oxidases which can be used in the present invention include glucose oxidase (EC 1. 1. 3. 4; the optimum pH is approx. 5.6), cholesterol oxidase (EC 1. 1. 3. 6; the optimum pH is approx. 5.8), uricase (EC 1. 7. 3. 3; the optimum pH is approx. 7.5–8.0), sarcosine oxidase (EC 1. 5. 3. 1; the optimum pH is approx. 7.0–9.0), lactate oxidase, pyruvate oxidase, glutamate oxidase, glycerol oxidase, bilirubin oxidase, etc.

In addition to the above-mentioned oxidases, there can be used oxidases described in Japanese Publication No. 56(1981)-45599, Japanese Patent Provisional Publications No. 53(1978)-24893 (GB 1,590,738) and No. 57(1982)-208998 and Japanese Patent Application No. 57(1982)-165233 (Japanese Patent Provisional Publication No. 59(1984)-54962 and EP 0 103 903 A2), etc. and a combination of different enzymes including these oxidases. If desired, these oxidases can be used in combination with a cofactor and/or a coenzyme.

The oxidase-containing layer is a layer containing oxidase (optionally in combination with a cofactor and/or a coenzyme) dispersed or dissolved in a hydrophilic polymer binder having film-forming property. As the hydrophilic polymer binder for the preparation of the oxidase-containing layer, there can be used any of the aforementioned hydrophilic polymer binders for the indicator layer. A representative hydrophilic polymer binder is gelatin. The dry thickness (thickness in dry state) of the oxidase-containing layer is within the range of approx. 0.5 $\mu$m to 5 $\mu$m, preferably approx. 1 $\mu$m to 3 $\mu$m. The oxidase content of the oxidase-containing layer may vary depending on the kind of oxidase, but is generally within the range of approx. 1,000 to 100,000 U/m$^2$, preferably approx. 3,000 to 50,000 U/m$^2$. When glucose oxidase is used, the content is within the range of approx. 2,000 to 40,000 U/m$^2$, preferably approx. 4,000 to 30,000 U/m$^2$.

There can be incorporated in the oxidase-containing layer a pH buffer capable of maintaining the layer at the optimum pH value for the oxidase or in the vicinity thereof. As the pH buffer, there can be used any of the known pH buffers described in the aforementioned literatures and patent specifications. When there is a great difference in pH value between the indicator layer and the oxidase-containing layer, an acidic polymer containing carboxyl or sulfonic groups or a basic polymer described in Japanese Patent Applications No. 58(1983)-17542 (Japanese Patent Provisional Publication No. 59(1984)-143959 and EP 0 116 361 A2) and No. 58(1983)-118594, etc. can be incorporated as a pH bufferring agent into at least one layer.

A cationic mordant can be incorporated into the oxidase-containing layer. When the aqueous liquid sample is blood, or more particularly a hemolyzed blood (whole blood, plasma or serum), the cationic mordant incorporated in the oxidase-containing layer can greatly reduce or substantially remove the interference of the hydrogen peroxide-decomposition active substances such as catalase or particularly hemoglobin. As the cationic mordant, there can be used conventional cationic polymers containing ammonium group, phosphonium group or sulfonium group used in silver halide color photographic materials or in the registration layer (detection layer) or migration-inhibiting layer (diffusion-preventing layer) of the multilayer analytical elements described in Japanese Patent Publication No. 58(1983)-18628, Japanese Patent Provisional Publications No. 53(1978)-72622 (U.S. Pat. No. 4,199,362), No. 54(1979)-29700 (U.S. Pat. No. 416,093), No. 54(1979)-138432 (U.S. Pat. No. 4,256,827) and No. 56(1981)-19454 (EP 0 022 673A and EP 0 031 842A), etc. Ammonium group-containing cationic polymer mordants are preferred, and examples thereof include styrene/p-[(N-benzyl-N,N-dimethylammonio)methyl]-styrene/divinylbenzene copolymer, styrene/p-[(1-methyl-1-piperidinio)methyl]styrene/divinylbenzene copolymer, etc. (counter anions are chlorine anions, etc.). The mordant can be used in an amount of approx. 5 to 200% by weight, preferably approx. 20 to 100% by weight based on the amount of the hydrophilic polymer binder. Even when the oxidase layer contains the cationic mordant, the dry thickness of the oxidase layer is within the range of approx. approx. 0.5 $\mu$m to 5 $\mu$m, preferably approx. 1 $\mu$m to 3 $\mu$m.

The oxygen-permeable, protein-impermeable light-blocking layer (hereinafter often referred to simply as light-blocking layer) is provided on the oxidase-containing layer (or the oxidase-containing layer further containing a cationic mordant). The term "oxygen-permeable, protein-impermeable" used herein means that oxygen ($O_2$) in air can substantially permeate through the layer, but proteins substantially do not permeate through the layer, when water serving as a solvent of the aqueous liquid sample penetrates into this layer to wet or swell this layer under analytical conditions. The term "protein" used herein refers to common proteins having a molecular weight of approx. 5,000 or higher, particularly conjugated proteins having hydrogen peroxide-decomposition activity such as catalase (having a molecular weight of approx. 250,000) and heme-protein, typically hemoglobin (having a molecular weight of approx. 65,000). The oxygen-permeable, protein-impermeable light-blocking layer is usually a nonporous layer which comprises a small amount of a light-blocking fine powder dispersed in a hydrophilic (or weakly hydrophilic) polymer binder having film-forming property. In the measurement of the color generated or changed in the indicator layer by reflection photometry from the side of the transparent (light-transmissive) support, the light-blocking layer blocks the color of the aqueous liquid sample spotted on the spreading layer mentioned later, particularly red color originating from hemoglobin in the case that whole blood is used. Moreover, the light-blocking layer functions as a light-reflecting layer as well as a background layer.

Examples of the light-blocking fine powders include fine titanium dioxide powder, fine barium sulfate powder, carbon black, fine aluminum powder or flake, etc. Among them, fine titanium dioxide powder and fine barium sulfate powder are preferable.

Examples of the hydrophilic (or weakly hydrophilic) polymer binders having film-forming property include gelatin (such as acid-treated gelatin, deionized gelatin, etc.), gelatin derivatives (such as phthalated gelatin, hydroxymethyl acrylate-grafted gelatin, etc.), polyvinyl alcohol, regenerated cellulose, cellulose acetate (such as cellulose diacetate), etc. Among them, gelatin and gelatin derivatives are preferable. Gelatin and gelatin derivatives can be used together with a conventional hardener (i.e., cross-linking agent). When these polymers are used for the preparation of an adhesive layer mentioned later, various hydrophilic polymers can be used as the polymer binders for the light-blocking layer like the indicator layer.

The ratio of the light-blocking fine powder to the polymer binder (dry basis) in the light-blocking layer can vary, provided that the produced light-blocking layer is so non-porous that the layer can allow permeation of oxygen but does not allow permeation of protein (the term "non-porous" includes such a microporous structure that the size of the pore or void is smaller than the average size with which the spreading effect or metering effect occurs in the porous spreading layer occurs). Specifically, the ratio of the light-blocking fine powder to the polymer binder (dry basis) can be within the range of approx. 10:2.5 to 10:7.5, preferably approx. 10:3.0 to 10:6.5, by volume. When the light-blocking fine powder is a fine titanium dioxide powder, the ratio of the fine titanium dioxide powder to the polymer binder (dry basis) is within the range of approx. 10:0.6 to 10:1.8, preferably approx. 10:0.8 to 10:1.5 by weight. The thickness of the light-blocking layer is be within the range of approx. 3 $\mu$m to 30 $\mu$m, preferably approx. 5 $\mu$m to 20 $\mu$m, on the dry basis.

If necessary, an intermediate layer can be provided between the indicator layer and the oxidase-containing layer and also between the oxidase-containing layer and the light-blocking layer. For the preparation of these intermediate layers, hydrophilic polymers having film-forming property similar to those used for the indicator layer can be used. The thickness of the intermediate layer can be within the range of approx. 0.2 $\mu$m to 10 $\mu$m, preferably approx. 0.5 $\mu$m to 7 $\mu$m.

If necessary, an adhesive layer can be provided between the light-blocking layer and the porous spreading layer (described later). For the preparation of the adhesive layer, there can be used hydrophilic polymers which have film-forming property similar to those used for the indicator layer and which can bond the porous spreading layer and the light-blocking layer to form an integrated structure when the adhesive layer is wetted or swollen with water. The thickness of the adhesive layer can be within the range of approx. 0.5 $\mu$m to 20 $\mu$m, preferably approx. 1 $\mu$m to 10 $\mu$m. Preferred hydrophilic polymers employable for the preparation of the intermediate layer and the adhesive layer include gelatin, gelatin derivatives, polyacrylamide, and polyvinyl alcohol.

If necessary, a surfactant can be incorporated into the indicator layer, the oxidase-containing layer or the oxidase-containing layer futher containing a cationic mordant, the light-blocking layer, the intermediate layer, and the adhesive layer. As the surfactant, a nonionic surfactant, particularly a nonionic surfactant containing 8 to 15 oxyethylene or oxypropylene units in the linear chain structure is preferred. If desired, known additives such as a hardener (cross-linking agent), a softening agent, a plasticizer, etc. can be further incorporated into these layers.

On the light-blocking layer, the porous spreading layer or a porous layer (patch) having a definite surface area is provided directly or through an adhesive layer. As the porous spreading layer, there can be adopted a non-fibrous isotropic porous medium layer described in Japanese Patent Publication No. 53(1978)-21677 (U.S. Pat. No. 3,992,158), Japanese Patent Provisional Publications No. 55(1980)-90859 (U.S. Pat. No. 4,258,001) and No. 58(1983)-123458, etc.; a fabric spreading layer described in Japanese Patent Provisional Publications No. 55(1980)-164356 and No. 57(1982)-66359, etc.; and a layer composed of a paper sheet containing a polyolefin polymer filament pulp described in Japanese Patent Provisional Publication No. 57(1982)-148250. As the porous layer having a definite surface, there can be adopted a porous material described in Japanese Utility Model Provisional Publication No. 57(1982)-42951 (DE 31 33 538A), etc. Among them, the spreading layer is preferred. Among various spreading layers, more preferred are a membrane filter layer (i.e., blushed polymer layer), a three-dimensional lattice-particulate structure layer formed by bonding polymer beads to one another under point contact with a polymer adhesive which is not swollen with water, and the fabric spreading layer. The spreading layer and the porous layer having a definite surface can be provided according to the methods described in the aforementioned patent specifications.

A surfactant, preferably the aforementioned nonionic surfactant, can be incorporated into the porous spreading layer (hereinafter often referred to simply as spreading layer), if necessary. Further, part of a reagent containing an enzyme such as cholesterol esterase can be incorporated into the porous spreading layer as described in Japanese Patent Publication No. 55(1980)-45599. The light-blocking fine powder can be also incorporated into the porous spreading layer.

The integral multilayer element for chemical analysis prepared by laminating the aforementioned layers to form the integrated structure is then cut in an appropriate size and encased in a slide frame described in Japanese Patent Provisional Publications No. 54(1979)-156079 (U.S. Pat. No. 4,169,751), No. 57(1982)-63452, and No. 58(1983)-501144 (WO-83/00391), Japanese Utility Model Provisional Publications No. 56(1981)-142454 (U.S. Pat. No. 4,387,990) and No. 58(1983)-32350, etc., whereby the element can be conveniently used as an analytical slide. Alternatively, the multilayer analytical element can be used in the form of a long tape or used by sticking it to a cut piece on an aperture card or putting it therein.

The multilayer analytical element of the present invention can be used for performing quantitative analyses for analytes present in aqueous liquid samples by the principle of colorimetric analysis method according to the methods described in the aforementioned patent specifications and the literature "Clinical Chemistry", 24 (8), 1335-1342(1979), etc.

The following examples are provided to further illustrate the present invention.

EXAMPLE 1

The surface of a smooth, transparent polyethylene terephthalate (PET) film having a gelatin subbing layer and a thickness of 180 μm was coated with the following indicator layer composition in the form of an aqueous solution in such an amount as to provide an indicator layer having a dry thickness of approx. 15 μm on the film, and dried.

| | |
|---|---|
| Peroxidase | 25,000 IU |
| 1,7-Dihydroxynaphthalene | 5 g |
| 4-Aminoantipyrine | 5 g |
| Gelatin | 200 g |
| Polyoxyethylene nonylphenyl ether | 5 g |

The surface of the indicator layer was coated with the following glucose oxidase layer composition in the form of an aqueous solution in such an amount as to provide a glucose oxidase layer having a dry thickness of approx. 2 μm on the indicator layer, and dried.

| | |
|---|---|
| Gelatin | 4.6 g |
| Glucose oxidase | 4,000 IU |
| Polyoxyethylene nonylphenyl ether | 0.1 g |

The surface of the glucose oxidase layer was then coated with the following light-blocking layer composition in the form of an aqueous dispersion in such an amount as to provide an oxygen-permeable, protein-impermeable light-blocking layer having a dry thickness of approx. 7 μm on the glucose oxidase layer, and dried.

| | |
|---|---|
| Fine titanium dioxide powder | 100 g |
| Gelatin | 10 g |

The surface of the light-blocking layer was then coated with the following adhesive layer composition in the form of an aqueous solution in such an amount as to provide an adhesive layer having a dry thickness of approx. 2 μm on the light-blocking layer, and dried.

| | |
|---|---|
| Gelatin | 10 g |
| Polyoxyethylene nonylphenyl ether | 0.1 g |

Water was then supplied in an amount of about 30 g/m² over the whole surface of the adhesive layer to wet the layers, and a 100% cotton broadcloth (100 count twin broadcloth) was superposed thereon under weak pressure. The resulting laminated structure was dried to prepare an integral multilayer element for chemical analysis employable for quantitative determination of glucose content.

COMPARISON EXAMPLE 1

The procedure of Example 1 was repeated except that the glucose oxidase layer was omitted and the surface of the indicator layer was coated with the following composition in the form of an aqueous dispersion in such an amount as to provide a glucose oxidase-containing light-blocking layer having a dry thickness of approx. 7 μm on the indicator layer instead, and dried to prepare a chemical analytical slide (comparison slide 1) for the use in quantitative determination of glucose content.

| | |
|---|---|
| Fine titanium dioxide powder | 10 g |
| Gelatin | 1 g |
| Glucose oxidase | 2,000 IU |

8 μl of human plasma was spotted as an aqueous liquid sample on each of the two kinds of the obtained chemical analytical slides under the conditions that the glucose concentration was kept unchanged but the hemoglobin concentration was varied to five different levels as shown in Table 1. The slide was then incubated at 37° C. for 6 minutes. Immediately, the optical density of the generated color was measured by reflection photometry from the side of the PET film (central wavelength of measurement: 500 nm). The results are set forth in Table 1.

TABLE 1

| Chemical Analytical Slide | Hemoglobin Concentration, mg/dl | | | | |
|---|---|---|---|---|---|
| | 0 | 50 | 100 | 500 | 1000 |
| Ex. 1 (Present Invention) | 0.95 | 0.95 | 0.95 | 0.94 | 0.93 |
| Comparison Slide 1 | 0.85 | 0.85 | 0.75 | 0.69 | 0.61 |

Remark: The optical density value means a value obtained by deducting a fogged optical density value (value obtained by conducting photometry in the same manner as that described above by using 7% aqueous albumin solution containing no glucose) from a photometrically measured value.

It is apparent from the results of Table 1 that the optical density value observed on the comparison slide 1 was lower than that of the analytical slide of the present invention even at the zero hemoglobin concentration level. Further, in the comparison slide 1, a negative error caused by the interference of hydrogen peroxide-decomposing activity of hemoglobin was observed with increase in the hemoglobin concentration. In contrast, in the analytical element of the present invention, there was observed little interference of hemoglobin and high optical density values were obtained, irrespective of whether hemoglobin was present or not.

COMPARISON EXAMPLE 2

The procedure of Example 1 was repeated except that the glucose oxidase layer was omitted and the film was coated with the following indicator layer composition in the form of an aqueous solution in such an amount as to provide an indicator layer having a dry thickness of approx. 15 μm instead, and dried to prepare a slide (comparison slide 2) for the use in quantitative determination of glucose content.

| | |
|---|---|
| Glucose oxidase | 2,500 IU |

-continued

| | |
|---|---|
| Peroxidase | 2,500 IU |
| 1,7-Dihydroxynaphthalene | 0.5 g |
| 4-Aninoantipyrine | 0.5 g |
| Gelatin | 20 g |
| Polyoxyethylene nonylphenyl ether | 0.2 g |

The amount of glucose oxidase per unit area contained in the indicator layer of the comparison slide was approximately equal to the amount (in terms of activity ratio) of glucose oxidase contained in the glucose analysis slide of Example 1 according to the present invention. 8 μl of human plasma containing glucose at different concentrations (the original content 86 mg/dl and added glucose amount) was spotted on each of the glucose analysis slide of the present invention and the comparison slide 2 under the conditions that the glucose concentration was varied to five different levels as set forth in Table 2. The slide was then incubated at 37° C. for 6 minutes. Immediately, the optical density of the generated color was measured by reflection photometry from the side of the PET film (central wavelength of measurement: 500 nm). The photometry results are set forth in Table 2.

TABLE 2

| Chemical Analytical Slide | Hemoglobin Concentration, mg/dl | | | | | |
|---|---|---|---|---|---|---|
| | 86 | 155 | 299 | 486 | 555 | 699 |
| Ex. 1 (Present Invention) | 0.38 | 0.57 | 0.86 | 1.00 | 1.10 | 1.21 |
| Comparison Slide 2 | 0.37 | 0.55 | 0.84 | 0.97 | 0.97 | 0.96 |

Remark: The optical density value means a value obtained by deducting a fogged optical density value (value obtained by conducting photometry in the same manner as that described above by using 7% aqueous albumin solution containing no glucose) from a photometrically measured value.

It is apparent from the results of Table 2 that in the comparison slide 2, the upper limit of the measurable range of glucose concentration was 486 mg/dl or below and the optical density value on the generated color was low. In contrast, in the chemical analytical slide of the present invention, the upper limit of the measurable range of glucose concentration was at least 699 mg/dl, the optical density value of the generated color was high and the slope of calibration curve was steep so that analytical accuracy was high. Further, it is clear from the results that the glucose concentration-measurable range of the chemical analytical slide of the present invention was approx. 1.5 times or more as wide as that of the comparison slide.

EXAMPLE 2

The procedure of Example 1 was repeated except that the film was coated with the following glucose oxidase layer composition in the form of an aqueous solution in such an amount as to provide a cationic polymer mordantcontaining glucose oxidase layer having a dry thickness of approx. 2 μm, and dried to prepare a glucose analysis slide.

| | |
|---|---|
| Gelatin | 3.0 g |
| Styrene/p-[(1-methyl-1-piperadinio)-methyl]styrene/divinylbenzene copolymer | 1.5 g |
| Glucose oxidase | 4,000 IU |
| Polyoxyethylene nonylphenyl ether | 0.1 g |

Using each of the glucose analysis slides of Examples 1 and 2 and performing the measurements in the same manner as in these examples, there were obtained a relationship between the hemoglobin concentration and the optical density value on the generated color (Table 3) and a relationship between the glucose concentration and the optical density value on the generated color (Table 4).

TABLE 3

Hemoglobin Concentration vs. Optical Density Value of Generated Color (glucose concentration was kept at the same level)

| Chemical Analytical Slide | Hemoglobin Concentration, mg/dl | | | | |
|---|---|---|---|---|---|
| | 0 | 50 | 100 | 500 | 1000 |
| Example 2 | 0.98 | 0.98 | 0.98 | 0.98 | 0.97 |
| Example 1 | 0.95 | 0.95 | 0.95 | 0.94 | 0.93 |

TABLE 4

Glucose Concentration vs. Optical Density Value of Generated Color

| Chemical Analytical Slide | Hemoglobin Concentration, mg/dl | | | | | |
|---|---|---|---|---|---|---|
| | 86 | 155 | 299 | 486 | 555 | 699 |
| Example 2 | 0.40 | 0.60 | 0.91 | 1.15 | 1.22 | 1.36 |
| Example 1 | 0.38 | 0.57 | 0.86 | 1.00 | 1.10 | 1.21 |

Remark: The optical density value (Tables 3 and 4) means a value obtained by deducting a fogged optical density value (value obtained by conducting photometry in the same manner as that described above by using 7% aqueous albumin solution containing no glucose) from a photometrically measured value.

It is apparent from the results of Tables 3 and 4 that the chemical analytical slide having the cationic mordant-containing glucose oxidase layer of the present invention was hardly disturbed by interference caused by the hydrogen peroxide-decomposing activity of hemoglobin, as compared with the chemical analytical slide having the glucose oxidase layer containing no cationic mordant. Thus, there was observed substantially no negative error originating from the interference in the analytical slide of the invention. Moreover, in the analytical slide having the mordant-containing glucose oxidase layer according to the invention, the optical density value on the generated color was high and the slope of calibration value was steep so that analytical accuracy was high, and further that the glucose concentration-measurable range was widened.

We claim:

1. An integral multilayer element for chemical analysis of glucose in a liquid sample, which comprises, in the following order:
   (a) a porous spreading layer;
   (b) an oxygen-permeable, protein-impermeable light-blocking layer;
   (c) a layer containing glucose oxidase;
   (d) an indicator layer containing peroxidase and an indication for hydrogen peroxide showing a photometrically detectable change in the presence of peroxidase and hydrogen peroxide; and
   (e) a water-impermeable, light-transmissive support.

2. The integral multilayer element of claim 1 wherein said light-blocking layer comprises a light-blocking titanium dioxide powder dispersed in a hydrophilic polymer binder, the ratio of the titanium dioxide powder to said polymer binder being within the range of from about 10:0.6 to 10:1.8 by weight.

3. The integral multilayer element of claim 1 wherein said porous spreading layer is made of fabric.

4. The integral multilayer element of claim 1 wherein said layer containing glucose oxidase comprises a glucose oxidase and a hydrophilic polymer.

5. The integral multilayer element of claim 1 wherein said layer containing glucose oxidase comprises a glucose oxidase, a cationic mordant, and a hydrophilic polymer.

* * * * *